(12) United States Patent
Yokoi et al.

(10) Patent No.: US 8,741,227 B2
(45) Date of Patent: Jun. 3, 2014

(54) ISOLATOR

(75) Inventors: Yasuhiko Yokoi, Ota (JP); Jiro Ohnishi, Ota (JP); Shinji Fukui, Gunma-ken (JP); Akifumi Iwama, Tsukuba (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 1165 days.

(21) Appl. No.: 12/693,969

(22) Filed: Jan. 26, 2010

(65) Prior Publication Data

US 2010/0189607 A1 Jul. 29, 2010

(30) Foreign Application Priority Data

Jan. 26, 2009 (JP) ................................. 2009-014765

(51) Int. Cl.
*A61L 2/00* (2006.01)
*A61L 9/00* (2006.01)
*B01L 1/04* (2006.01)
*B01D 47/00* (2006.01)
*A61L 2/02* (2006.01)
*A61L 2/20* (2006.01)
*A61L 2/22* (2006.01)
*A61L 9/015* (2006.01)
*F24F 13/28* (2006.01)
*B01D 45/00* (2006.01)

(52) U.S. Cl.
CPC ............... *A61L 9/00* (2013.01); *A61L 2/0017* (2013.01); *A61L 2/022* (2013.01); *A61L 2/208* (2013.01); *A61L 2/22* (2013.01); *A61L 9/015* (2013.01); *F24F 13/28* (2013.01); *B01D 45/00* (2013.01)
USPC ........... 422/298; 422/292; 422/305; 422/306; 96/121; 96/227; 96/243; 96/397; 96/417; 96/424; 454/187; 454/228

(58) Field of Classification Search
CPC ......... A61L 9/00; A61L 2/0017; A61L 2/022; A61L 2/208; A61L 2/22; A61L 9/015; F24F 13/28; B01D 45/00
USPC ................... 422/3, 5, 28, 105, 119, 292, 298, 422/305–306; 96/121, 227, 243, 397, 417, 96/424; 454/187, 228
See application file for complete search history.

(56) References Cited

U.S. PATENT DOCUMENTS 5,173,258 A 12/1992 Childers

FOREIGN PATENT DOCUMENTS

| JP | 2006-068122 | * | 3/2006 | ................ A61L 2/20 |
| JP | 2010-051351 A | | 3/2010 | |

(Continued)

OTHER PUBLICATIONS

Japanese Patent Office machine English translation of the Detailed Description section of JP 2006-068122.*

(Continued)

*Primary Examiner* — Monzer R Chorbaji
(74) *Attorney, Agent, or Firm* — McDermott Will & Emery LLP (57) ABSTRACT

An isolator includes a workroom having a first sterilizing material supply port, a first sterilizing material discharge port, a first gas supply port and a first gas discharge port, a sterilization chamber having a second sterilizing material supply port, a second sterilizing material discharge port, a second gas supply port and a second gas discharge port, a sterilizing material supply unit, a first sterilizing material supply path connecting the sterilizing material supply unit to the first sterilizing material supply port, a second sterilizing material supply path connecting the sterilizing material supply unit to the second sterilizing material supply port, a first circulating path connecting the first sterilizing material discharge port to the sterilizing material supply unit, a second circulating path connecting the second sterilizing material discharge port to the sterilizing material supply unit, a first gas supply path, a second gas supply path, a first gas discharge path, a second gas discharge path, and a control unit.

8 Claims, 2 Drawing Sheets

(56) References Cited

FOREIGN PATENT DOCUMENTS

| WO | WO 2005/036151 | A2 | 4/2005 |
| WO | WO 2008/116341 | A2 | 10/2008 |

OTHER PUBLICATIONS

European Search Report issued in European Patent Application No. EP 10000769.9 dated Apr. 14, 2010.

* cited by examiner

ISOLATOR

This application is based upon and claims the benefit of priority from the prior Japanese Patent Applications No. 2009-014765, filed on Jan. 26, 2009, the entire contents of which are incorporated herein by reference.

BACKGROUND OF THE INVENTION

1. Field of the Invention

The present invention relates to a bio isolator.

2. Description of the Related Art

A bio isolator, an isolator for bio research, a biohazard isolator or the like is a system having a sterilized workroom, in which operations that require a sterile environment, such as those involving biologically-derived materials obtained by cell culture, for instance, are performed. The sterile environment meant here is an environment substantially free of dust and germs such that it allows no entry of substances other than the materials used in the work done in the workroom. Among conventionally known technologies for such an environment is an isolator having a sterilization chamber which is connected to a workroom via a door and in which articles to be carried into the workroom are sterilized.

The workroom is equipped with a gas supply port and a gas discharge port. Air outside the isolator is supplied into the workroom through the gas supply port, and the air in the workroom is discharged through a gas discharge port. Generally, the isolator is provided with a particulate trap filter, such as a HEPA (High-Efficiency Particulate Air) filter, at the gas supply port in order to keep a sterile environment for the workroom, and the outside air is supplied into the workroom through the particulate trap filter. Also, a particulate trap filter is provided at the gas discharge port, and the air inside the workroom is discharged outside through the particulate trap filter.

Also, in the isolator, a sterilization treatment is conducted in the workroom and the sterilization chamber with a sterilizing material (sterilizing agent), such as hydrogen peroxide gas, sprayed into them.

Under the circumstances as described above, the present inventors have realized the following problems with the system:

In the above-mentioned sterilization treatment, upon completion of sterilization process, a process of replacing the sterilizing material in the workroom with air is carried out, in which the sterilizing material therein is decomposed by a catalyst while air is sent thereinto. At this time, if there is the sterilizing material adsorbed by the particulate trap filter, the replacement process will take a long time because it is not easy to remove the sterilizing material from the particulate trap filter. As a consequence, the process of sterilization as a whole takes a long time.

The isolator is of such design that work in the workroom cannot be started until the concentration of the sterilizing material is low enough to have no adverse effect on the articles to be processed. Besides, in the isolator, after the end of one operation in the workroom, a sterilization treatment is generally performed before the start of the next operation. Hence, if the work efficiency in the isolator is to be enhanced, it is necessary to shorten the time required by the sterilization treatment.

SUMMARY OF THE INVENTION

The present invention has been made based on such realization of the inventors, and a purpose thereof is to provide a technology that can shorten the time required by the sterilization treatment by an isolator.

An isolator according to one embodiment of the present invention comprises: a workroom in which a work involving biologically-derived materials is performed, the workroom including a first sterilizing material supply port, a first sterilizing material discharge port, a first gas supply port provided with a particulate trap filter, and a first gas discharge port provided with a particulate trap filter; a sterilization chamber for communicating with the workroom via a door in which an article to be carried into the workroom is sterilized, said sterilization chamber including a second sterilizing material supply port, a second sterilizing material discharge port, a second gas supply port provided with a particulate trap filter, and a second gas discharge port provided with a particulate trap filter; a sterilizing material supply unit for supplying a sterilizing material to the workroom and the sterilization chamber; a first sterilizing material supply path for connecting the sterilizing material supply unit to the first sterilizing material supply port without the medium of the particulate trap filter; a second sterilizing material supply path for connecting the sterilizing material supply unit to the second sterilizing material supply port without the medium of the particulate trap filter; a first circulating path for connecting the first sterilizing material discharge port to the sterilizing material supply unit without the medium of the particulate trap filter; a second circulating path for connecting the second sterilizing material discharge port to the sterilizing material supply unit without the medium of the particulate trap filter; a first gas supply path for connecting the exterior to the first gas supply port; a second gas supply path for connecting the exterior to the second gas supply port; a first gas discharge path for connecting the first gas discharge port to the exterior; a second gas discharge path for connecting the second gas discharge port to the exterior; and a control unit for controlling the switching of flow paths for the sterilizing material and gas taken in from the exterior.

It is to be noted that any arbitrary combinations or rearrangement, as appropriate, of the aforementioned constituting elements and so forth are all effective as and encompassed by the embodiments of the present invention.

BRIEF DESCRIPTION OF THE DRAWINGS

Embodiments will now be described by way of examples only, with reference to the accompanying drawings which are meant to be exemplary, not limiting and wherein like elements are numbered alike in several Figures in which.

DETAILED DESCRIPTION OF THE INVENTION

The invention will now be described by reference to the preferred embodiments. This does not intend to limit the scope of the present invention, but to exemplify the invention.

Hereinbelow, the embodiments will be described with reference to the accompanying drawings. Note that in each Figure the same reference numerals are given to the same components and the description thereof is omitted as appropriate.

Moreover, the embodiments given are for illustrative purposes only and all features and their combination thereof described in the present embodiment are not necessarily essential to the invention.

(First Embodiment)

Figure 1:
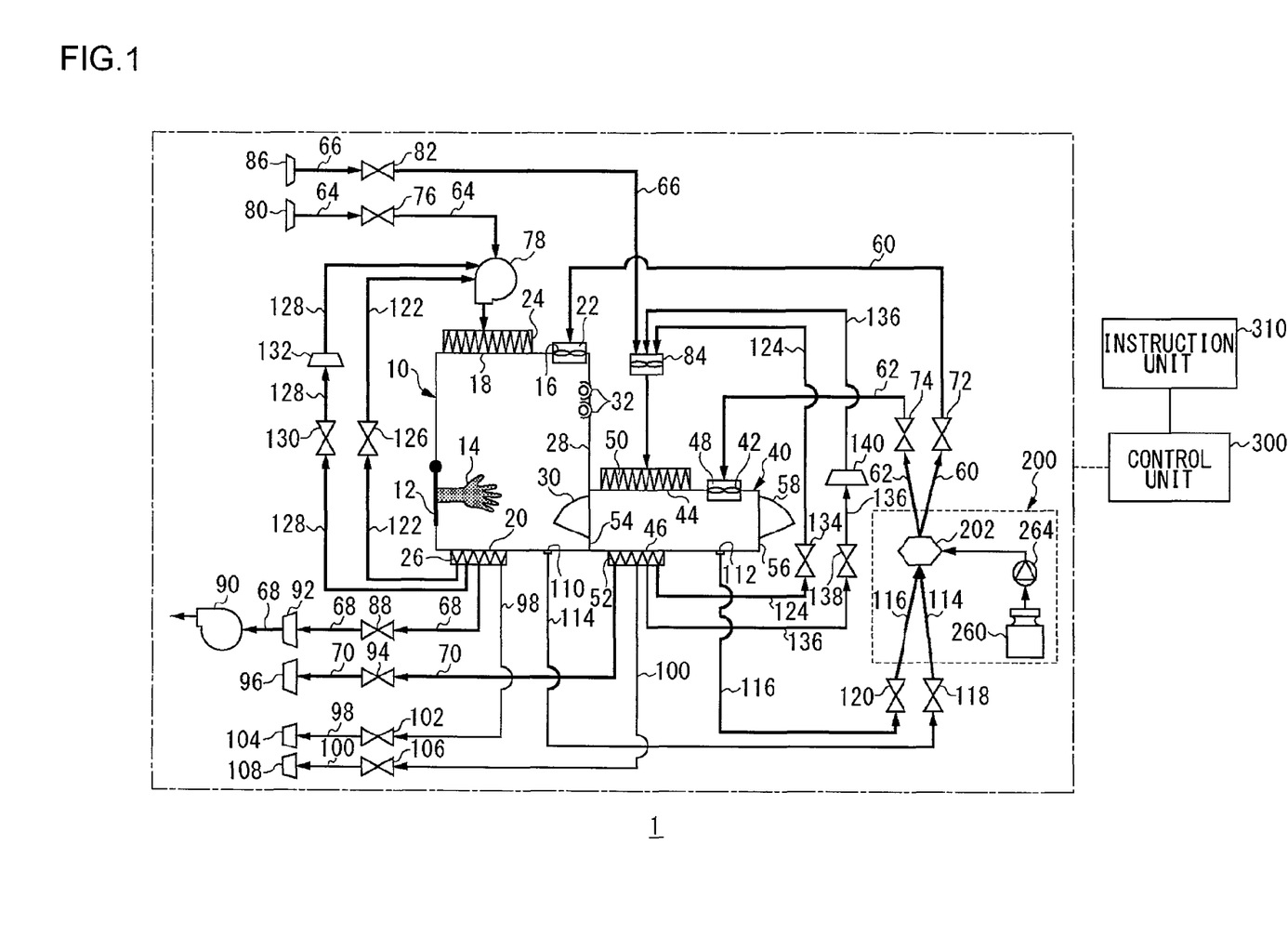
FIG. 1 is a schematic diagram showing a structure of an isolator according to a first embodiment of the present invention.

FIG. 1 is a schematic representation showing a structure of an isolator according to a first embodiment of the present invention.

As shown in FIG. 1, an isolator 1 of the first embodiment includes a workroom 10, a sterilization chamber 40, a sterilizing material supply unit 200, and a control unit 300.

The workroom 10 is a space in which work involving biologically-derived materials, such as cell extraction or cell culture, for instance, is performed. The workroom 10 is provided with a front door 12 which is openable and closable, and a work glove 14 to be used in operations in the workroom 10 is installed in a predetermined position of the front door 12. A worker can insert his/her hand into the work glove 14 through a not-shown opening provided in the front door 12 and perform work in the workroom 10 via the work glove 14. Note that biologically-derived materials meant here are materials such as living organisms themselves including cells, substances constituting the living organisms, and substances produced by the living organisms.

The workroom 10 is equipped with a first sterilizing material supply port 16, a first gas supply port 18, and a first gas discharge port 20. The first sterilizing material supply port 16 is provided with a fan 22. The first gas supply port 18 and the first gas discharge port 20 are provided with a HEPA (High-Efficiency Particulate Air) filter 24 and a HEPA filter 26, respectively. It is to be noted that the first sterilizing material supply port 16 is not provided with a HEPA filter. Also, an opening is provided in a side wall 28 of the workroom 10, which is the wall on the side where the sterilization chamber 40 is located, and a door 30 is openably and closably disposed in such a manner as to cover the opening. Further, the workroom 10 is provided with a lighting 32 which illuminates the interior of the workroom 10.

The sterilization chamber 40 is a space in which articles, such as culturing tools, culture media and the like, to be carried into the workroom 10 are sterilized. The sterilization chamber 40 is equipped with a second sterilizing material supply port 42, a second gas supply port 44, and a second gas discharge port 46. The second sterilizing material supply port 42 is provided with a fan 48. Also, the second gas supply port 44 and the second gas discharge port 46 are provided with a HEPA filter 50 and a HEPA filter 52, respectively. It is to be noted that the second sterilizing material supply port 42 is not provided with a HEPA filter. Also, an opening is provided in a side wall 54 of the sterilization chamber 40, which is the wall on the side where the workroom 10 is located, and the sterilization chamber 40 is so disposed that the opening thereof is aligned with the opening provided in the side wall 28 of the workroom 10. Thus the workroom 10 and the sterilization chamber 40 have their internal spaces communicating with each other via a door 30. Further, an opening through which articles are carried into the sterilization chamber 40 is provided in a side wall 56 of the sterilization chamber 40, and a carry-in door 58 is openably and closably disposed in such a manner as to cover the opening.

The sterilizing material supply unit 200 performs a function of supplying a sterilizing material (sterilizing agent) to the workroom 10 and the sterilization chamber 40. The isolator 1 can create a sterile environment in the workroom 10 and the sterilization chamber 40 by supplying the sterilizing material thereinto. Note that the sterile environment meant here is an environment substantially free of dust and germs such that it allows no entry of substances other than the materials used in the work done in the workroom. The sterilizing material supply unit 200 includes a sterilizing gas generator 202, a sterilizing material cartridge 260 for storing the raw material for the sterilizing material, and a pump 264 for supplying the raw material for the sterilizing material from the sterilizing material cartridge 260 to the sterilizing gas generator 202. In the present embodiment, the sterilizing material, or sterilant (sterilizing agent), is a hydrogen peroxide gas, and the raw material for the sterilizing material (sterilizing agent) is a water solution of hydrogen peroxide. It should be noted that the sterilizing material is not limited to hydrogen peroxide gas, but it may be a substance containing active oxygen species such as ozone.

Figure 2A:
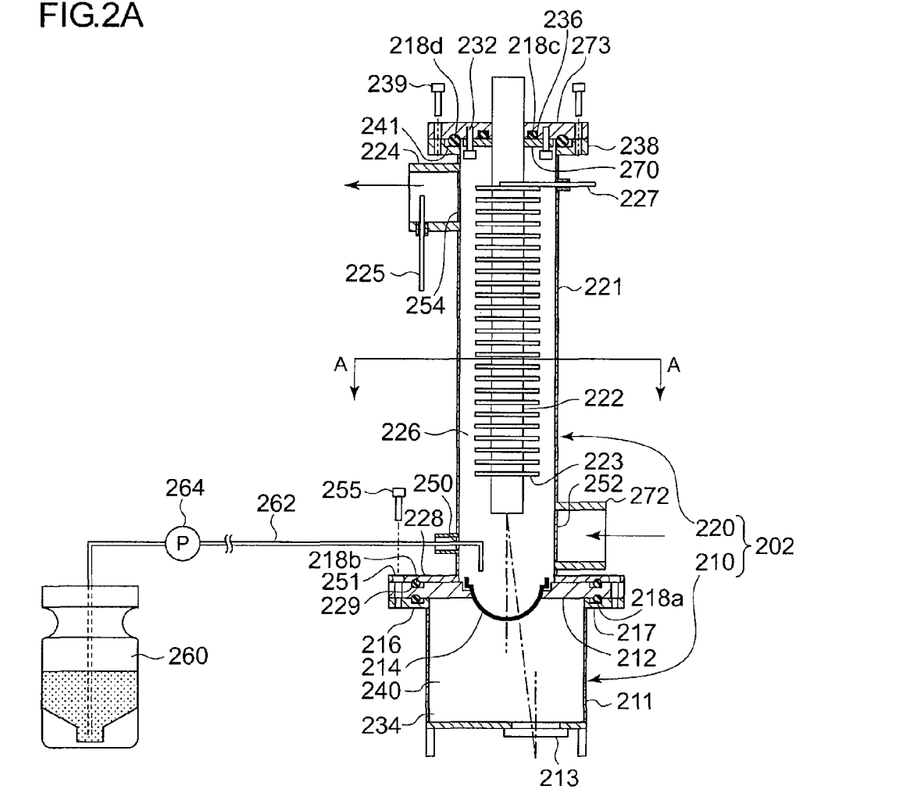
FIG. 2A is a schematic illustration showing a structure of a sterilizing material supply apparatus.
Figure 2B:
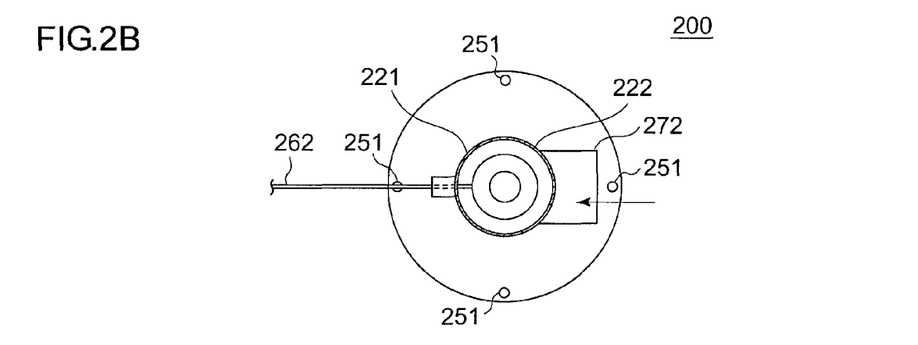
FIG. 2B is a cross-sectional view taken along the line A-A of FIG. 2A.

A detailed structure of the sterilizing material supply unit 200 will be explained by referring to FIGS. 2A and 2B. FIG. 2A is a schematic illustration showing a structure of the sterilizing material supply unit 200 according to the first embodiment. FIG. 2B is a cross-sectional view taken along the line A-A of FIG. 2A.

As shown in FIG. 2A, the sterilizing material supply unit 200 includes a sterilizing gas generator 202 which is comprised of a mist generation unit (atomizing unit) 210 and a vaporizing unit 220.

The mist generation unit 210 includes a holding member 211, a partition member 212, an ultrasonic vibrator 213, and a cup 214 serving as the storage unit.

The holding member 211 is a receptacle constituting the mist generation unit 210. The ultrasonic vibrator 213 is disposed on the bottom of the holding member 211. The ultrasonic vibrator 213 is a device that converts electrical energy into ultrasonic vibration. In the present embodiment, the ultrasonic vibrator 213 is not placed in the center of the bottom of the holding member 211 but in a position dislocated closer to an opening 252 to be described later.

A flange 216 is formed around the top periphery of the holding member 211. The top surface of the flange 216 is provided with a groove 217 into which an O-ring 218a is fitted.

The partition member 212 is disposed on top of the flange 216. The partition member 212 is a doughnut-shaped member with an opening formed in the middle thereof. The outside diameter of the partition member 212 is the same as that of the flange 216. The top surface of the partition member 212 is provided with a groove 229 into which an O-ring 218b is fitted.

The cup 214 is attached to the opening provided in the partition member 212, and the bottom of the cup 214 projects toward the ultrasonic vibrator 213. The cup 214 is made of a resin or with a metal sheet having a thickness of about 0.05 mm, for instance.

A space 234 enclosed by the holding member 211, the partition member 212, and the cup 214 is filled with an ultrasonic propagation liquid 240 which is used to propagate the ultrasonic vibration generated by the ultrasonic vibrator 213. Note that the liquid recommendable as the ultrasonic propagation liquid is water or similar liquid with low viscosity.

In the mist generation unit 210 configured as described above, the hydrogen peroxide solution supplied to the cup 214 is turned into a mist by the ultrasonic vibration propagated through the ultrasonic propagation liquid 240, and the hydrogen peroxide turned into mist is sent into the vaporizing unit 220. In this process, droplets of hydrogen peroxide adhering to the inside of the vaporizing unit 220 without becoming mist will drop to the cup 214 by the force of gravity and will be turned into mist again.

It should be appreciated here that the wavefront direction of the ultrasonic vibration generated by the ultrasonic vibrator 213 is preferably tilting about 7 degrees toward the cup 214. In such an arrangement, the water column by the hydrogen peroxide solution stored by the cup 214 rises up at a tilt, so that a stable atomization of the hydrogen peroxide solution can be accomplished.

The vaporizing unit 220, which is disposed above the mist generation unit 210, is comprised mainly of a heating pipe 221, a heater 222, a piping 224, and thermometers 225 and 227.

The heating pipe 221 is mounted on top of the holding member 211 in such a manner that its axial direction is vertical. To be more specific, the heating pipe 221 has a flange 228 formed around the lower end thereof. The outside diameter of the flange 228 is the same as those of the partition member 212 and the flange 216.

The flange 216, the partition member 212 and the flange 228 are provided with screw holes 251 in predetermined positions. The mist generation unit 210 and the vaporizing unit 220 are assembled by screwing screws 255 into the screw holes 251 with the O-rings 218a and 218b fitted in the grooves 217 and 229, respectively. Airtightness between the flange 216 and the partition member 212 is enhanced by the O-ring 218a. Also, airtightness between the flange 228 and the partition member 212 is enhanced by the O-ring 218b.

The heating pipe 221 has an opening 250 and an opening 252 in the lower part thereof. In the present embodiment, the opening 250 and the opening 252 are located in positions opposite to each other. Led through the opening 250 is the piping 262 which supplies the hydrogen peroxide solution stored in the sterilizing material cartridge 260 to the cup 214. Provided midway along the piping 262 is a pump 264 (e.g., Peristaltic pump) which is used to pump up the hydrogen peroxide solution stored in the sterilizing material cartridge 260.

On the other hand, a piping 272 is connected to the opening 252. And connected to the other end of the piping 272 are the downstream ends of a first circulating path 114 and a second circulating path 116.

Inside the heating pipe 221, a flow path 226 is formed where hydrogen peroxide and air flow from bottom upward.

In the present embodiment, the heating pipe 221 is disposed directly above the cup 214. Therefore, even when the hydrogen peroxide mist recombines into droplets within the heating pipe 221, they will drop down to the cup 214 by the force of gravity. The hydrogen peroxide having returned to the cup 214 will again be turned into a mist by the ultrasonic vibration and sent to the heating pipe 221. Thus, the hydrogen peroxide liquefied in the heating pipe 221 is returned to the cup 214 and turned into mist again by a simple structure, thereby accomplishing a complete gasification of hydrogen peroxide solution in the cup 214.

The heater 222 is disposed inside the heating pipe 221 along its axis. The heater 222 is regulated at a temperature of about 180° C. through the ON/OFF control by the control unit 300. The temperature of the heater 222 is detected by the thermometer 227, and the detected temperature is transmitted to the control unit 300. When the temperature of the heater 222 exceeds about 220° C., the control unit 300 cuts off power supply to the heater 222. Note that the heater 222 is preferably provided with a plurality of fins 223. Such an arrangement will promote gasification of hydrogen peroxide by increasing the contact area between the heater 222 and the hydrogen peroxide flowing through the flow path 226.

A flange (fin) 270 for fixation is provided in the upper part of the heater 222. A lid member 273 has a groove 236 formed along the periphery of the heater 222, and an O-ring 218c is fitted in this groove 236. Also, the lid member 273 is provided with an opening through which the upper portion of the heater 222 is inserted. The heater 222 is fastened to the lid member 273 by means of screws 232, and the O-ring 218c enhances airtightness between the flange 270 and the lid member 273.

The heating pipe 221 is provided with a flange 238 at the top portion of the heating pipe 221. The flange 238 has a groove 241 formed in its surface facing the lid member 273, and an O-ring 218d is fitted in this groove 241. The flange 238 is fastened to the lid member 273 by means of screws 239. In this manner, the lid member 273 is mounted on the heating pipe 221 with the O-ring 218d enhancing airtightness, and at the same time the state of the heater 222 inserted in the heating pipe 221 is maintained.

The heating pipe 221 has an opening 254 in a side face of the upper part of the heating pipe 221, to which one end of the piping 224 is connected. Provided on the piping 224 is the thermometer 225 which is used to measure the internal temperature of the piping 224. The internal temperature of the piping 224 measured by the thermometer 225 is transmitted to the control unit 300. Connected to the other end of the piping 224 are the upstream ends of a first sterilizing material supply path 60 and a second sterilizing material supply path 62.

Referring back to FIG. 1, the isolator 1 includes a first sterilizing material supply path 60, a second sterilizing material supply path 62, a first gas supply path 64, a second gas supply path 66, a first gas discharge path 68, and a second gas discharge path 70.

The first sterilizing material supply path 60 connects the sterilizing material supply unit 200 to the first sterilizing material supply port 16 without the medium of a HEPA filter. The first sterilizing material supply path 60 is provided with an on-off valve 72. The sterilizing material generated by the sterilizing material supply unit 200 is supplied into the workroom 10 through the first sterilizing material supply path 60 when the on-off valve 72 is open and the fan 22 is on.

The second sterilizing material supply path 62 connects the sterilizing material supply unit 200 to the second sterilizing material supply port 42 without the medium of a HEPA filter. The second sterilizing material supply path 62 is provided with an on-off valve 74. The sterilizing material generated by the sterilizing material supply unit 200 is supplied into the sterilization chamber 40 through the second sterilizing material supply path 62 when the on-off valve 74 is open and the fan 48 is on.

The first gas supply path 64 connects the exterior of the isolator 1 to the first gas supply port 18. Since the first gas supply port 18 is provided with the HEPA filter 24, the exterior of the isolator 1 and the workroom 10 are connected with each other via the HEPA filter 24. The first gas supply path 64 is provided with an on-off valve 76, and the end on the workroom 10 side of the first gas supply path 64 is connected to a blower 78. The blower 78 is so arranged as to blow gas toward the workroom 10, and a gas, such as air, which exists outside the isolator 1 (hereinafter referred to as "air") is supplied into the workroom 10 through the first gas supply path 64 when the on-off valve 76 is open and the blower 78 is on. Provided at an exterior end of the first gas supply path 64 is a sterilizing material decomposition treatment filter 80 containing a metallic catalyst, such as platinum, which prevents the sterilizing material from flowing back from the workroom 10 and out of the isolator 1.

The second gas supply path 66 connects the exterior of the isolator 1 to the second gas supply port 44. Since the second gas supply port 44 is provided with the HEPA filter 50, the exterior of the isolator 1 and the sterilization chamber 40 are connected with each other via the HEPA filter 50. The second gas supply path 66 is provided with an on-off valve 82, and the end on the sterilization chamber 40 side of the second gas supply path 66 is connected to a fan 84. The fan 84 is so arranged as to send air toward the sterilization chamber 40, and air from outside the isolator 1 is supplied into the sterilization chamber 40 through the second gas supply path 66 when the on-off valve 82 is open and the fan 84 is on. Provided at an exterior end of the second gas supply path 66 is a sterilizing material decomposition treatment filter 86 containing a metallic catalyst, such as platinum, which prevents the sterilizing material from flowing back from the sterilization chamber 40 and out of the isolator 1.

The first gas discharge path 68 connects a first gas discharge port 20 to the exterior of the isolator 1. Since the first gas discharge port 20 is provided with the HEPA filter 26, the workroom 10 and the exterior of the isolator 1 are connected with each other via the HEPA filter 26. The first gas discharge path 68 is provided with an on-off valve 88, and an exterior end of the first gas discharge path 68 is connected to a blower 90. The blower 90 is so arranged as to blow air toward the exterior of the isolator 1, and air inside the workroom 10 is discharged to the exterior of the isolator 1 through the first gas discharge path 68 when the on-off valve 88 is open and the blower 90 is on. Provided between the on-off valve 88 of the first gas discharge path 68 and the blower 90 is a sterilizing material decomposition treatment filter 92 containing a metallic catalyst, such as platinum, which prevents the sterilizing material from flowing from the workroom 10 to the exterior of the isolator 1.

The second gas discharge path 70 connects the second gas discharge port 46 to the exterior of the isolator 1. Since the second gas discharge port 46 is provided with the HEPA filter 52, the sterilization chamber 40 and the exterior of the isolator 1 and are connected with each other via the HEPA filter 52. The second gas discharge path 70 is provided with an on-off valve 94, and air inside the sterilization chamber 40 is discharged to the exterior of the isolator 1 through the second gas discharge path 70 when the on-off valve 94 is open and the fan 84 or the fan 48 is on. Provided at an exterior end of the second gas discharge path 70 is a sterilizing material decomposition treatment filter 96 containing a metallic catalyst, such as platinum, which prevents the sterilizing material from flowing from the sterilization chamber 40 to the exterior of the isolator 1.

Also, the isolator 1 includes a workroom pressure regulating flow path 98 and a sterilization chamber pressure regulating flow path 100.

The workroom pressure regulating flow path 98 connects the first gas discharge port 20 to the exterior of the isolator 1. The workroom pressure regulating flow path 98 is provided with an on-off valve 102, and air inside the workroom 10 is discharged to the exterior of the isolator 1 through the workroom pressure regulating flow path 98 when the on-off valve 102 is open and the blower 78 is on. The flow path diameter of the workroom pressure regulating flow path 98 is set smaller than that of the first gas supply path 64. Accordingly, the supply rate of air into the workroom 10 via the first gas supply path 64 is greater than the discharge rate of air from the workroom 10 via the workroom pressure regulating flow path 98. Therefore, when there is no outflow of air through the first gas discharge path 68 with the on-off valve 88 closed or when the total of the outflow of air through the first gas discharge path 68 and the outflow of air through the workroom pressure regulating flow path 98 is at a prescribed level or below, the pressure in the workroom 10 is maintained positive, thus preventing the entry of foreign matter into the workroom 10 from outside. Provided at an exterior end of the workroom pressure regulating flow path 98 is a sterilizing material decomposition treatment filter 104 containing a metallic catalyst, such as platinum, which prevents the sterilizing material from flowing from the workroom 10 to the exterior of the isolator 1.

The sterilization chamber pressure regulating flow path 100 connects the second gas discharge port 46 to the exterior of the isolator 1. The sterilization chamber pressure regulating flow path 100 is provided with an on-off valve 106, and air inside the sterilization chamber 40 is discharged to the exterior of the isolator 1 through the sterilization chamber pressure regulating flow path 100 when the on-off valve 106 is open and the fan 84 is on. The flow path diameter of the sterilization chamber pressure regulating flow path 100 is set smaller than that of the second gas supply path 66. Accordingly, the supply rate of air into the sterilization chamber 40 via the second gas supply path 66 is greater than the discharge rate of air from the sterilization chamber 40 via the sterilization chamber pressure regulating flow path 100. Therefore, when there is no outflow of air through the second gas discharge path 70 with the on-off valve 94 closed or when the total of the outflow of air through the second gas discharge path 70 and the outflow of air through the sterilization chamber pressure regulating flow path 100 is at a prescribed level or below, the pressure in the sterilization chamber 40 is maintained positive, thus preventing the entry of foreign matter into the sterilization chamber 40 from outside. Provided at an exterior end of the sterilization chamber pressure regulating flow path 100 is a sterilizing material decomposition treatment filter 108 containing a metallic catalyst, such as platinum, which prevents the sterilizing material from flowing from the sterilization chamber 40 to the exterior of the isolator 1.

The isolator 1 according to the present embodiment includes a first sterilizing material discharge port 110 provided in the workroom 10 and a second sterilizing material discharge port 112 provided in the sterilization chamber 40. Also, the isolator 1 includes a circulating path 114 that connects the first sterilizing material discharge port 110 to the sterilizing material supply port 200 without the medium of the HEPA filter and a second circulating path 116 that connects the second sterilizing material discharge port 112 to the sterilizing material supply unit 200 without the medium of the HEPA filter.

An end of the first circulating path 114 on a sterilizing material supply unit 200 side is coupled to the piping 272 (See FIG. 2A). Thus a flow path is formed such that the sterilizing material produced by the sterilizing material supply unit 200 is circulated in the order of the first sterilizing material supply path 60, the workroom 10, the first circulating path 114 and the sterilizing material supply unit 200. The first circulating path 114 is provided with an on-off valve 118. When the on-of valve 118 is open and the fan 22 is on, the sterilizing material in the workroom 10 is sent to the sterilizing supply unit 200 after it has passed through the first circulating path 114.

An end of the second circulating path 116 on a sterilizing material supply unit 200 side is coupled to the piping 272 (See FIG. 2A). Thus a flow path is formed such that the sterilizing material produced by the sterilizing material supply unit 200 is circulated in the order of the second sterilizing material supply path 62, the sterilization chamber 40, the second circulating path 116 and the sterilizing material supply unit 200. The second circulating path 116 is provided with an on-off valve 120. When the on-off valve 120 is open and the fan 48 is on, the sterilizing material in the sterilization chamber 40 is sent to the sterilizing material supply unit 200 after it has passed through the second circulating path 116.

The isolator 1 according to the present embodiment further includes a first filter circulating path 122, which is a first circulating path going through a filter, and a second filter circulating path 124, which is a second circulating path going through a filter.

The first filter circulating path 122 connects the first gas discharge port 20 to the first gas supply port 18, on the outside of the workroom 10. The first filter circulating path 122 is provided with an on-off valve 126. An end of the first filter circulating path 122 on a first gas supply port 18 side is coupled to the blower 78. When the on-off valve 126 is open and the blower 78 is on, the sterilizing material in the workroom 10 is circulated in the order of the first gas discharge port 20, the first filter circulating path 122, the first gas supply port 18 and the workroom 10. At this time, the sterilizing material passes through the HEPA filter 26 and the HEPA filter 24.

The first filter circulating path 122 includes a first decomposition treatment unit path 128 which is a path going through a decomposition treatment unit. The first decomposition treatment unit path 128 connects the first gas discharge port 20 to the first gas supply port 18, on the outside of the workroom 10. An end of the first decomposition treatment unit path 128 on a first gas supply port 18 side is coupled to the blower 78. The first decomposition treatment unit path 128 is provided with an on-off valve 130. Also, the first decomposition treatment unit path 128 is provided with a sterilizing material decomposition treatment filter 132 having a catalyst, such as platinum, which decomposes the sterilizing material. The sterilizing material decomposition treatment filter 132 constitutes a sterilizing material decomposition treatment unit. When the on-off valve 130 is open and the blower 78 is on, the sterilizing material in the workroom 10 is circulated in the order of the first gas discharge port 20, the first decomposition treatment unit path 128, the first gas supply port 18 and the workroom 10. In this process, the sterilizing material passes through the sterilizing material decomposition treatment filter 132 repeatedly so as to be decomposed. As a result, the concentration of the sterilizing material to be discharged outside can be further reduced.

The second filter circulating path 124 connects the second gas discharge port 46 to the second gas supply port 44, on the outside of the sterilization chamber 40. The second filter circulating path 124 is provided with an on-off valve 134. An end of the second filter circulating path 124 on a second gas supply port 44 side is coupled to the fan 84. When the on-off valve 134 is open and the fan 84 is on, the sterilizing material in the sterilization chamber 40 is circulated in the order of the second gas discharge port 46, the second filter circulating path 124, the second gas supply port 44 and the sterilization chamber 40. At this time, the sterilizing material passes through the HEPA filter 52 and the HEPA filter 50.

The second filter circulating path 124 includes a second decomposition treatment unit path 136 which is a path going through a decomposition treatment unit. The second decomposition treatment unit path 136 connects the second gas discharge port 46 to the second gas supply port 44, on the outside of the sterilization chamber 40. An end of the second decomposition treatment unit path 136 on a second gas supply port 44 side is coupled to the blower 84. The second decomposition treatment unit path 136 is provided with an on-off valve 138. Also, the second decomposition treatment unit path 136 is provided with a sterilizing material decomposition treatment filter 140 having a catalyst, such as platinum, which decomposes the sterilizing material. The sterilizing material decomposition treatment filter 140 constitutes a sterilizing material decomposition treatment unit. When the on-off valve 138 is open and the fan 84 is on, the sterilizing material in the sterilization chamber 40 is circulated in the order of the second gas discharge port 46, the second decomposition treatment unit path 136, the second gas supply port 44 and the sterilization chamber 40. In this process, the sterilizing material passes through the sterilizing material decomposition treatment filter 140 repeatedly so as to be decomposed. As a result, the concentration of the sterilizing material to be discharged outside can be further reduced.

The isolator 1 includes the control unit 300. The control unit 300 controls the opening and closing of each on-off valve and the ON/OFF of each blower and fan, and thereby controls the switching of the flow path of sterilizing material and air taken in from the outside. The control unit 300 also controls the generation of sterilizing material by the sterilizing material supply unit 200. The isolator 1 also includes an instruction unit 310 by which a user can select any of various sterilization processes and treatments described later. The control unit 300 has a not-shown storage which stores various kinds of control programs and conversion tables associating each on-off valve and fan with their respective states in each sterilization. The control unit 300 retrieves, from the storage, a control program and a conversion table associated with the sterilization treatment selected by the user, and controls the switching of flow paths according to said control program and conversion tale so as to conduct the selected sterilization treatment.

A description is now given of a sterilization treatment carried out in the isolator 1 configured as above. In a state where a work is being carried out in the workroom 10, the door 30 is closed at first. At this time, the control unit 300 turns on the on-off valves 76, 88 and 102, turns off the on-off valves 118, 126 and 130, and turns on the blower 78 and 90. As a result, the outside air is supplied into the workroom 10 through the first gas supply path 64. This creates a flow path where the air inside the workroom 10 is discharged to the exterior through the first gas discharge path 68 and the workroom pressure regulating flow path 98. The air blowing quantity of the blowers 78 and 90 is adjusted in such a manner that the quantity of air supplied into the workroom 10 from the exterior via the first gas supply path 64 thereof is greater than the quantity of air discharged from the workroom 10 via the first gas discharge path 68 and the workroom pressure regulating flow path 98. Thus the inside of the workroom 10 is maintained at a positive pressure.

A sterilization treatment done by the isolator 1 includes a pretreatment process, a sterilization process, and a replacement process. In the pretreatment process, a sterilizing material is supplied into the workroom 10 or the sterilization chamber 40 which is to be sterilized, so that the workroom 10 or the sterilization chamber 40 is filled with sterilizing material supplied. When the concentration of the sterilizing material in the workroom 10 or the sterilization chamber 40 in the pretreatment process reaches a required concentration level or above, the sterilization process for sterilizing the interior of the workroom 10 or the sterilization chamber 40 starts. As the sterilization process is completed after a predetermined duration of time has elapsed, the replacement process starts. In the replacement process, the sterilizing material is discharged from the workroom 10 or the sterilization chamber 40 and is decomposed by a catalyst, so that the concentration thereof drops. At the same time, the inside of the workroom 10 or the sterilization chamber 40 is replaced with the outside air.

The isolator 1 according to the present embodiment has a first sterilization treatment for sterilizing the interior of the workroom 10 and a second sterilization treatment for sterilizing the interior of the sterilization chamber 40 as the sterilization treatment, and can conduct the first sterilization treatment and the second sterilization treatment independently of each other. Thus, the isolator 1 can sterilize the workroom 10 and the sterilization chamber 40 independently of each other. It is to be noted here that the first sterilization treatment and the second sterilization treatment can be conducted in parallel with each other. In other words, when either one of the sterilization treatments is in progress, the other sterilization treatment can be executed whilst the current sterilization treatment is underway. Note that the second sterilization treatment can be conducted not only when the sterilization chamber 40 is sterilized but also when articles to be carried into the workroom 10 is sterilized.

(First Sterilization Treatment: the Sterilization of a Workroom)

As the control unit 300 receives an instruction to execute the first sterilization treatment from the instruction unit 310, the control unit 300 has the first sterilization treatment conducted. At first, the control unit 300 starts a pretreatment process with the front door 12 and the door 30 closed. In the pretreatment process, the sterilizing material supply unit 200 starts to generate and supply a sterilizing material, and the on-off valves 76, 88, 102, 118, 126 and 130 are closed and the blowers 78 and 90 are turned off. Then, with the on-off valve 72 open and the fan 22 turned on, the sterilizing material is supplied into the workroom 10 by way of the first sterilizing material supply path 60. When the workroom 10 is filled with the sterilizing material and the concentration of the sterilizing material becomes equal to or greater than a concentration level required for the sterilization of the interior of the workroom 10, the pretreatment process is terminated.

As the pretreatment process is terminated, the control unit 300 starts a process of sterilization. In the process of sterilization, the on-off valve 118 is opened and the gas inside the workroom 10 including the sterilizing material is sent to the sterilizing material supply unit 200 via the first circulating path 114. Thus a circulating path is formed such that the sterilizing material is circulated in the order of the first sterilizing material supply path 60, the workroom 10, the first circulating path 114 and the sterilizing material supply unit 200. After a predetermined duration of time has elapsed or the consumption of the raw material for sterilizing material has reached a prescribed level, the process of sterilization is terminated. For example, the process of sterilization may be terminated when the sterilizing material cartridge 260 becomes empty.

As the process of sterilization is terminated, the control unit 300 starts a replacement process. In the replacement process, the sterilizing material supply unit 200 stops the generation and supply of the sterilizing material, and the on-off valve 88 is opened and the blower 90 is turned on. Thus, air inside the workroom 10 including the sterilizing material is discharged to the first gas discharge path 68. Also, the on-off valve 76 is opened and the blower 78 is turned on, so that air outside the isolator 1 is supplied into the workroom 10. In this manner, the sterilizing material in the workroom 10 is replaced by the air. Also, the sterilizing materials in the first sterilizing material supply path 60 and the first circulating path 114 are removed and replaced by the air. The air discharged to the first gas discharge path 68 is discharged outside the isolator 1 by way of the first gas discharge path 68. When the air passes through the sterilizing material decomposition treatment filter 92, the sterilizing material contained in the air is decomposed by the sterilizing material treatment filter 92.

Note that the arrangement may be such that the sterilizing material is also discharged to the workroom pressure regulating flow path 98 with the on-off valve 102 open.

When the concentration of the sterilizing material in the workroom 10 becomes a prescribed level or below in the replacement process, the replacement process is terminated and the workroom 10 is ready to be used. Here, the concentration of the sterilizing material for which the workroom 10 can be ready to be used corresponds to a concentration with which a biologically-derived material used in the work is processed without being affected normegligibly. If the sterilizing material is a hydrogen peroxide gas, this level of concentration will be less than or equal to 1 ppm time weighted average (TWA) which is specified by the American Conference of Governmental Industrial Hygienists (ACGIH). The concentration of the sterilizing material in the workroom 10 can be obtained if a sensor such as an infrared absorption sensor is installed in the workroom 10. Alternatively, whether the concentration of the sterilizing material in the workroom 10 reaches a prescribed value or not may be detected in a manner such that the time until when the concentration of the sterilizing material in the workroom 10 reaches the prescribed value is calculated and the passage of such time is monitored.

(Second Sterilization Treatment: the Sterilization of a Sterilization Chamber)

As the control unit 300 receives an instruction to execute the second sterilization treatment from the instruction unit 310, the control unit 300 has the second sterilization treatment conducted. At first, the control unit 300 starts a pretreatment process with the door 30 and the carry-in door 58 closed and articles being carried into the sterilization chamber 40 if the articles are to be sterilized. In the pretreatment process, the sterilizing material supply unit 200 starts to generate and supply the sterilizing material, and the on-off valves 82, 94, 106, 120, 134 and 138 are closed and the fan 84 is turned off. Then, with the on-off valve 74 open and the fan 48 turned on, the sterilizing material is supplied into the sterilization chamber 40 by way of the second sterilizing material supply path 62. When the sterilization chamber 40 is filled with the sterilizing material and the concentration of the sterilizing material becomes equal to or greater than a concentration level required for the sterilization of the interior of the sterilization chamber 40 or required for the sterilization of the articles carried into the workroom 10.

As the pretreatment process is terminated, the control unit 300 starts a process of sterilization. In the process of sterilization, the on-off valve 120 is opened and the gas inside the sterilization chamber 40 including the sterilizing material is sent to the sterilizing material supply unit 200 via the second circulating path 116. Thus a circulating path is formed such that the sterilizing material is circulated in the order of the second sterilizing material supply path 62, the sterilization chamber 40, the second circulating path 116 and the sterilizing material supply unit 200. After a predetermined duration of time has elapsed or the consumption of the raw material for the sterilizing material has reached a prescribed level, the process of sterilization is terminated. For example, the process of sterilization may be terminated when the sterilizing material cartridge 260 runs out.

As the process of sterilization is terminated, the control unit 300 starts a replacement process. In the replacement process, the sterilizing material supply unit 200 stops the generation and supply of the sterilizing material, and the on-off valve 94 is opened. Thus, air inside the sterilization chamber 40 including the sterilizing material is discharged to the second gas discharge path 70. Also, the on-off valve 82 is opened and the fan 84 is turned on, so that air outside the isolator 1 is supplied into the sterilization chamber 40. In this manner, the sterilizing material in the sterilization chamber 40 is replaced by the air. Also, the sterilizing materials in the second sterilizing material supply path 62 and the second circulating path 116 are removed and replaced by the air. The air discharged to the second gas discharge path 70 is discharged outside the isolator 1 by way of the second gas discharge path 70. When the air passes through the sterilizing material decomposition treatment filter 96, the sterilizing material contained in the air is decomposed by the sterilizing material treatment filter 96. Note that the arrangement may be such that the sterilizing material is also discharged to the sterilization chamber pressure regulating flow path 100 with the on-off valve 106 open.

When the concentration of the sterilizing material in the sterilization chamber 40 becomes a prescribed level or below in the replacement process, the replacement process is terminated and the door 30 or the side wall 56 can be opened, namely, the sterilization chamber 40 is ready to be opened. Here, the concentration of the sterilizing material for which the sterilization chamber 40 is openable corresponds to a concentration with which a worker or a biologically-derived material is not adversely affected even if the sterilizing material is released to the exterior of the isolator 1 or released to the interior of the workroom 10. This level of concentration is less than or equal to 1 ppm time weighted average (TWA) which is specified by the American Conference of Governmental Industrial Hygienists (ACGIH). The concentration of the sterilizing material in the sterilization chamber 40 can be obtained if a sensor such as an infrared absorption sensor is installed in the sterilization chamber 40. Alternatively, whether the concentration of the sterilizing material in the sterilization chamber 40 reaches a prescribed value or not may be detected in a manner such that the time until when the concentration of the sterilizing material in the sterilization chamber 40 reaches the prescribed value is calculated and the passage of such time is monitored.

(Third Sterilization Treatment: the Sterilization of Workroom and Sterilization Chamber)

The isolator 1 according to the present embodiment has a third sterilization treatment for sterilizing the interior of the workroom 10 and the interior of the sterilization chamber 40 at the same time, as the sterilization treatment. As the control unit 300 receives an instruction to execute the third sterilization treatment from the instruction unit 310, the control unit 300 has the third sterilization treatment conducted. At first, the control unit 300 starts a pretreatment process with the front door 12 and the carry-in door 58 closed and the door 30 open. In the pretreatment process, the sterilizing material supply unit 200 starts to generate and supply a sterilizing material, and the on-off valves 74, 76, 82, 88, 94, 102, 106, 118, 120, 126, 130, 134 and 138 are closed and the blowers 78 and 90 and the fans 48 and 84 are turned off. Then, with the on-off valve 72 open and the fan 22 turned on, the sterilizing material is supplied into the workroom 10 by way of the first sterilizing material supply path 60. The sterilizing material supplied into the workroom 10 is moved into the sterilization chamber 40 through the door 30 and thereby the sterilizing material is supplied to the interiors of the workroom 10 and the sterilization chamber 40. When the concentration of the sterilizing material becomes equal to or greater than concentration levels required for the sterilization of the interiors of the workroom 10 and the sterilization chamber 40, the pretreatment is terminated.

As the pretreatment process is terminated, the control unit 300 starts a process of sterilization. In the process of sterilization, the on-off valve 120 is opened and the gas inside the sterilization chamber 40 including the sterilizing material is sent to the sterilizing material supply unit 200 via the second circulating path 116. Thus a circulating path is formed such that the sterilizing material is circulated in the order of the first sterilizing material supply path 60, the workroom 10, the sterilization chamber 40, the second circulating path 116 and the sterilizing material supply unit 200, thereby sterilizing the workroom 10 and the sterilization chamber 40. After a predetermined duration of time has elapsed or the consumption of the raw material for sterilizing material has reached a prescribed level, the process of sterilization is terminated. For example, the process of sterilization may be terminated when the sterilizing material cartridge 260 becomes empty.

As the process of sterilization is terminated, the control unit 300 starts a replacement process. In the replacement process, the sterilizing material supply unit 200 stops the generation and supply of the sterilizing material, and the on-off valves 88 and 94 are opened and the blower 90 and the fan 84 are turned on. Thus, gas inside the workroom 10 and sterilization chamber 40 including the sterilizing material is discharged to the first gas discharge path 68 and the second gas discharge path 70. Also, the on-off valves 76 and 82 are opened and the blower 78 is turned on, so that air outside the isolator 1 is supplied into the workroom 10 and the sterilization chamber 40. In this manner, the sterilizing material in the workroom 10 and the sterilization chamber 40 is replaced by the air. Also, the sterilizing materials in the first sterilizing material supply path 60 and the second circulating path 116 are removed and replaced by the air. The sterilizing material discharged to the first gas discharge path 68 and the second gas discharge path 70 is decomposed by the sterilizing material decomposition treatment filter 92 and the sterilizing material decomposition treatment filter 96. Note that the arrangement may be such that the sterilizing material is also discharged to the workroom pressure regulating flow path 98 and the sterilization chamber pressure regulating flow path 100 with the on-off valves 102 and 106 open.

When the concentration of the sterilizing materials in the workroom 10 and the sterilization chamber 40 becomes a prescribed level or below in the replacement process, the replacement process is terminated.

Note that the delivery of the sterilizing material into the sterilizing material supply unit 200 via the second circulating path 116 and the delivery of the sterilizing material to thereinto via the first circulating path 114 may be conducted in parallel with each other or in a switchable manner. Hence, the supply rate of the sterilizing material into the workroom 10 can be made to differ from that of the sterilizing material into the sterilization chamber 40, so that the degrees of sterilization can be adjusted in the workroom 10 and the sterilizing chamber 40 separately. Specifically, in the initial stage of the process of sterilization, for instance, the sterilizing material mainly moves from the first sterilizing material supply port 16 toward the first sterilizing material discharge port 110 due to the circulation of the sterilizing material via the first circulating path 114. Accordingly, the main flow of the sterilizing material is so formed as to pass through the workroom 10 only. Then, when the flow of the sterilizing material is switched, after a predetermined duration of time, from the circulation via the first circulating path 114 to the circulation via the second circulating path 116, the sterilizing material mainly moves from the first sterilizing material supply port 16 toward the second sterilizing material discharge port 112. Accordingly, the main flow of the sterilizing material is so formed as to pass through the sterilization chamber 40 also.

As a result, the sterilization of interior of the workroom 10 can be conducted in a more concentrated manner.

Alternatively, in the initial stage of the process of sterilization, the main flow of the sterilizing material passing through the workroom 10 and another flow thereof branching out from this main flow into the sterilization chamber 40 are formed in a manner such that the circulation of the sterilizing material via the first circulating path 114 and the circulation thereof via the second circulating path 116 are carried out in parallel with each other. Since the position at which the sterilizing material is supplied is the first sterilizing material supply port 16, the amount of sterilizing material passing through within the workroom 10 is larger than that entering into the sterilization chamber 40. Then, the circulation of the sterilizing material via the first circulating path 114 is shut off after a predetermined duration of time, so that the main flow of the sterilizing material is so formed as to pass through the interior of the sterilization chamber 40. Thus the amount of sterilizing material supplied into the sterilization chamber 40 can be increased as compared with the case when the switching is made between the first circulating path 114 and the second circulating path 116, and the sterilization of the interior of the workroom 10 can be conducted in a more concentrated manner.

Also, in the pretreatment process, the sterilizing material may be supplied into the sterilization chamber 40 via the second sterilizing material supply path 62 and move into the workroom 10 through the door 30. In the process of sterilization, the sterilizing material may be circulated in the order of the second sterilizing material supply path 62, the sterilizing chamber 40, the workroom 10, the first circulating path 114, and the sterilizing material supply unit 200. In such a case, if the circulation of the sterilizing material via the circuit circulating path 114 and the circulation thereof via the second circulating path 116 are conducted in parallel with each other or in a switchable manner, the supply rate of the sterilizing material into the workroom 10 can be made to differ from that of the sterilizing material into the sterilization chamber 40. As a result, the degrees of sterilization can be adjusted in the workroom 10 and the sterilizing chamber 40 separately.

As the sterilizing material passes through the HEPA filter, part of the sterilizing material is adsorbed by the HEPA filter. The sterilizing material adsorbed by the HEPA filter is not easily removed from the HEPA filter and strips off gradually over a comparatively long period of time. Thus, if the sterilizing material remains in the HEPA filter 24 disposed on an air inlet side of the workroom 10, for instance, there is a possibility that the sterilizing material may strip off from the HEPA filter 24 during the work in the workroom 10 and the sterilizing material stripped off may be mixed into the workroom 10. In order to assure the removal of such sterilizing material from the HEPA filter, the time for the replacement process needs to be set longer. In contrast to this, in the above-described first sterilization treatment, the second sterilization treatment and the third sterilization treatment, the sterilizing material is supplied into the workroom 10 and the sterilization chamber 40 without the medium of the HEAP filter 24 disposed on the inlet side of the workroom 10 and the HEPA filter 50 disposed on the inlet side of the sterilization chamber 40. Thus the time for the replacement process can be made shorter as compared with the case where the sterilizing material passes through the HEPA filters. As a result, the time required for the sterilization treatment can be reduced.

(The Sterilization of HEPA Filters)

In the above-described first sterilization treatment or the third sterilization treatment, the sterilizing material does not pass through the HEPA filter 24, so that there are cases where the HEPA filter 24 may not be sufficiently sterilized. In the light of this potential problem, the isolator 1 can conduct the following sterilizing treatment to sterilize the HEPA filter 24. This filter sterilization treatment is conducted after either the first sterilization treatment or the third sterilization treatment is selected and the user selects the sterilization treatment of the HEPA filter 24. Also, this filter sterilization treatment may be selected as a fourth sterilization treatment combined with the first sterilization treatment or a fifth sterilization treatment combined with the third sterilization treatment.

As the filter sterilization treatment of the HEPA filter 24 is selected, the control unit 300 has the sterilizing material supplied into the workroom 10 circulated, with predetermined timing, by way of the filter circulating path 122 in the first sterilization treatment or the third sterilization treatment. More specifically, in a sterilization process of the first sterilization treatment or the third sterilization treatment, the on-off valve 126 is opened with predetermined timing and the blower 78 is turned on. This causes the gas including the sterilizing material in the workroom 10 to circulate in the order of the HEPA filter 26, the first filter circulating path 122, the HEPA filter 24 and the workroom 10 so as to sterilize the HEPA filter 24.

Similarly, in the above-described second sterilization treatment or the third sterilization treatment, the sterilizing material does not pass through the HEPA filter 50, so that there are cases where the HEPA filter 50 may not be sufficiently sterilized. In the light of this potential problem, the isolator 1 can conduct the following sterilizing treatment to sterilize the HEPA filter 50. This filter sterilization treatment is conducted after either the second sterilization treatment or the third sterilization treatment is selected and the user selects the sterilization treatment of the HEPA filter 50. Also, this filter sterilization treatment may be selected as a sixth sterilization treatment combined with the second sterilization treatment, a seventh sterilization treatment combined with the third sterilization treatment, or an eighth sterilization treatment combined with the fifth sterilization treatment.

As the filter sterilization treatment of the HEPA filter 50 is selected, the control unit 300 has the sterilizing material supplied into the sterilization chamber 40 circulated, with predetermined timing, by way of the second filter circulating path 124 in the second sterilization treatment or the third sterilization treatment. More specifically, in a sterilization process of the second sterilization treatment or the third sterilization treatment, the on-off valve 134 is opened with predetermined timing and the fan 84 is turned on. This causes the gas including the sterilizing material in the sterilization chamber 40 to circulate in the order of the HEPA filter 52, the second filter circulating path 124, the HEPA filter 50 and the sterilization chamber 40 so as to sterilize the HEPA filter 50.

Furthermore, in the above-described filter sterilization treatment of the HEPA filter 24, the control unit 300 has the sterilizing material supplied into the workroom 10 circulated, with predetermined timing, by way of the first decomposition treatment unit path 128. More specifically, in a sterilization process of the first sterilization treatment or the third sterilization treatment, the sterilizing material is circulated by way of the first filter circulating path 122; then the on-off valve 130 is opened with predetermined timing and the on-off valve 126 is closed. This causes the air including the sterilizing material in the workroom 10 to circulate in the order of the HEPA filter 26, the first decomposition treatment unit path 128, the HEPA filter 24 and the workroom 10, and causes the sterilizing material to repeatedly pass through the sterilizing material decomposition treatment filter 132 so as to be decomposed and removed. As the concentration of the sterilizing material in the workroom 10 becomes a prescribed value or below, the control unit 300 terminates the process of sterilization and starts the replacement process.

Similarly, in the above-described filter sterilization treatment of the HEPA filter 50, the control unit 300 has the sterilizing material supplied into the sterilization chamber 40 circulated, with predetermined timing, by way of the second decomposition treatment unit path 136. More specifically, in a sterilization process of the second sterilization treatment or the third sterilization treatment, the sterilizing material is circulated by way of the second filter circulating path 124; then the on-off valve 138 is opened with predetermined timing and the on-off valve 134 is closed. This causes the air including the sterilizing material in the sterilization chamber 40 to circulate in the order of the HEPA filter 52, the second decomposition treatment unit path 136, the HEPA filter 50 and the sterilization chamber 40, and causes the sterilizing material to repeatedly pass through the sterilizing material decomposition treatment filter 140 so as to be decomposed and removed. As the concentration of the sterilizing material in the sterilization chamber 40 becomes a prescribed value or below, the control unit 300 terminates the process of sterilization and starts the replacement process.

Suppose that the sterilizing material is not subjected to the above-described decomposition and removal prior to the replacement process. Then the decomposition of the sterilizing material in the sterilizing material decomposition treatment filter 92 and the sterilizing material decomposition treatment filter 96 will take a long time. This is because the concentration of the sterilizing material is high in the initial stage of the replacement process. In the process of sterilization according to the present embodiment, on the other hand, the sterilizing material is decomposed after the gas in the workroom 10 passes through the first decomposition treatment unit path 128 repeatedly and the gas in the sterilization chamber 40 passes through the second decomposition treatment unit path 136 repeatedly. Therefore, the sterilizing material in the workroom 10 or the sterilization chamber 40 can be reduced in a shorter time, and consequently the time for sterilization treatment can be shortened. Also, the gas inside the workroom 10 or the sterilization chamber 40 is discharged to the exterior of the isolator 1 after the concentration of the sterilizing material has been sufficiently reduced. Thus, the leak of the sterilizing material to the exterior can be prevented more reliably. Note that the "prescribed value" is the value capable of both reducing the sterilizing material treatment time and preventing the leak of the sterilizing material, for example, and may be set based on the experiments and the results of simulation runs.

When the above-described filter sterilization treatment is conducted, the sterilizing material passes through the HEPA filter 24 and the HEPA filter 50 disposed on the air inlet side. Thus the replacement process takes a longer time than when no filter sterilization treatment is conducted. In the light of this, for example, where one operation has been completed in the workroom and then a sterilization treatment is to be conducted before the start of the next operation, the first sterilization treatment, the second sterilization treatment, or the third sterilization treatment is conducted. Consequently, the time for sterilization treatment can be shortened and the next operation can be started earlier. On the other hand, for example, where one-day-long operation is over and the next operation is scheduled to be conducted the next day, or where periodic maintenance work is to be done, not only the first sterilization treatment, the second sterilization treatment, or the third sterilization treatment but also the filter sterilizing treatment is conducted. Consequently, the filters disposed on the air inlet side are also sterilized and therefore the reliability of work done in the isolator 1 can be enhanced.

In the first sterilization treatment and the third sterilization treatment, the sterilizing material supplied into the workroom 10 passes through an air-outlet-side HEPA filter 26, so that part of the sterilizing material is adsorbed by the HEPA filter 26. It takes a comparatively long period of time to remove the sterilizing material adsorbed by the HEPA filter 26. However, it is less likely that the sterilizing material flows back into the workroom 10. This is because the sterilizing material stripped off from the HEPA filter 26 is carried along by the flow of air flowing during an operation from the workroom 10 to the exterior of the isolator 1 and is sent out to a first gas discharge path 68 side. Accordingly, if no filter sterilization treatment is conducted, the time for sterilization treatment can be shortened, regardless of whether there is any sterilizing material adsorbed by the HEPA filter 26 or not, when compared with the case where a filter sterilization treatment is conducted.

To sum up the operations of and the advantageous effects achieved by the arrangement thus far explained, the isolator 1 according to the first embodiment is provided with the first sterilizing material supply path 60 which connects the sterilizing material supply unit 200 to the workroom 10 without the medium of a HEPA filter and the second sterilizing material supply path 62 which connects the sterilizing material supply unit 200 to the sterilization chamber 40 without the medium of a HEPA filter. Hence, the interiors of the workroom and the sterilization chamber can be sterilized without the intervention of HEPA filters disposed on the air inlet side of the workroom and the sterilization chamber. This shortens the time required for the sterilization process because the time until the concentration of the sterilizing material reaches a predetermined level in the pretreatment process is shortened and the time for the replacement process is also shortened. Furthermore, the interiors of the workroom and the sterilization chamber can be sterilized more completely because there is reduced wasteful consumption of sterilizing material due to its adsorption to the HEPA filters.

Also, the isolator 1 is provided with the first circulating path 114 which connects the workroom 10 to the sterilizing material supply unit 200 without the medium of a HEPA filter and the second circulating path 116 which connects the sterilization chamber 40 to the sterilizing material supply unit 200 without the medium of a HEPA filter. Hence, the sterilizing material can be sent out to the sterilizing material supply unit without the intervention of HEPA filters disposed on an air outlet side of the workroom and the sterilization chamber. Accordingly, a circulating path can be formed without the intervention of a HEPA filter between the workroom and the sterilizing material supply unit or between the sterilization chamber and the sterilizing material supply unit. This allows sterilization of the interiors of the workroom and the sterilization chamber with improved sterilization efficiency, thus improving the reliability of the isolator.

Also, the isolator 1 is provided with the first gas supply path 64 and the first gas discharge path 68, which connect the exterior and the workroom 10 to each other, and the second gas supply path 66 and the second gas discharge path 70, which connect the exterior and the sterilization chamber 40 to each other. As a result, the sterilizing material inside the workroom and the sterilization chamber can be removed more rapidly and reliably. This will further improve the reliability of the isolator.

Also, the isolator 1 is of such design that the first sterilization treatment, in which the interior of the workroom 10 is sterilized by supplying the sterilizing material thereto via the first sterilizing material supply path 60, and the second sterilization treatment, in which the interior of the sterilization chamber 40 is sterilized by supplying the sterilizing material thereto via the second sterilizing material supply path 62, can be conducted independently of each other. Therefore, it is possible to conduct the sterilization of the workroom and that of the sterilization chamber by staggering their starting hours. For example, a sterilization in the sterilization chamber is started while work is going on in the workroom and if the work in the workroom is completed while the sterilization in the sterilization chamber is still going on, then another sterilization in the workroom can be started without waiting for the completion of sterilization in the sterilization chamber. This will lead to an improvement in the work efficiency in the isolator and an increase in the production of the processed articles.

Also, in the isolator 1, the third sterilization treatment described herein can be conducted. For example, the third sterilization treatment is defined such that, with the door 30 open, the sterilizing material is supplied into the workroom 10 via the first sterilizing material supply path 60 and the sterilizing material having moved from the workroom 10 to the sterilization chamber 40 is sent to the sterilizing material supply unit 200 via the second circulating path 116. Or the third sterilization treatment is defined such that the sterilizing material is supplied into the sterilization chamber 40 via the second sterilizing material supply path 62 and the sterilizing material having moved from the sterilization chamber 40 to the workroom 10 is sent to the sterilizing material supply unit 200 via the first circulating path 114. In this manner, the workroom and the sterilization chamber can be sterilized together. Also, when the sterilizing material is supplied via the first sterilizing material supply path 60, the sterilizing material is sent out via the second circulating path 116, and when the sterilizing material is supplied via the second sterilizing material supply path 62, the sterilizing material is sent out via the first circulating path 114. Thus, the flow of the sterilizing material can be created from the workroom to the sterilization chamber or from the sterilization chamber to the workroom. This helps to accomplish reliable sterilization in both of the workroom and the sterilization chamber.

Also, in the third sterilization treatment of the isolator 1, the sterilizing material is supplied into the workroom 10 and the sterilization chamber 40 via the first sterilizing material supply path 60, and the delivery of the sterilizing material via the second circulating path 116 back to the sterilizing material supply unit 200 and the delivery of the sterilizing material via the first circulating path 114 back to the sterilizing material supply unit 200 are performed in parallel with each other or in a switchable manner. Thus, the supply rate of the sterilizing material into the workroom can be made to differ from that of the sterilizing material into the sterilization chamber, so that the degrees of sterilization can be adjusted in the workroom and the sterilizing chamber separately. Hence, an optimum sterilization treatment can be conducted according to the state of isolator operation.

Also, the isolator 1 is provided with the first filter circulating path 122 which connects the first gas discharge port 20 to the first gas supply port 18 of the workroom 10. In the first sterilization treatment or the third sterilization treatment of the isolator 1, the sterilizing material supplied to the workroom 10 is circulated by way of the first filter circulating path 122 with predetermined timing. Also, the isolator 1 is provided with the second filter circulating path 124 which connects the second gas discharge port 46 to the second gas supply port 44 of the sterilization chamber 40. In the second sterilization treatment or the third sterilization treatment of the isolator 1, the sterilizing material supplied to the sterilization chamber 40 is circulated by way of the second filter circulating path 124 with predetermined timing. Thus the HEPA filters disposed on the air inlet side of the workroom and the sterilization chamber can be sterilized, so that the interiors of the workroom and the sterilization chamber can be more reliably maintained sterile.

Also, the first filter circulating path 122 includes the first decomposition treatment unit path 128 which goes through the sterilizing material decomposition treatment filter 132. And in the first sterilization treatment of the isolator 1, the sterilizing material supplied to the workroom 10 is circulated by way of the first decomposition treatment unit path 128 with predetermined timing. Also, the second filter circulating path 124 includes the second decomposition treatment unit path 136 which goes through the sterilizing material decomposition treatment filter 140. And in the second sterilization treatment of the isolator 1, the sterilizing material supplied to the sterilization chamber 40 is circulated by way of the second decomposition treatment unit path 136 with predetermined timing. As a result, the sterilizing material in the workroom and the sterilization chamber is decomposed by passing through the respective sterilizing material decomposition treatment filters repeatedly. Therefore, the sterilizing material can be reduced in a shorter time, and consequently the time for sterilization treatment can be shortened. Also, the leak of the sterilizing material to the exterior can be prevented more reliably, thus raising the safety of the isolator.

The present invention is not limited to the above-described embodiments only, and it is understood by those skilled in the art that various modifications such as changes in design may be made based on their knowledge and the embodiments added with such modifications are also within the scope of the present invention.

For example, the valves to be used are not limited to on-off valves, but they may be three-way valves. Also, an opening/closing detection sensor may be provided at the door 30, and the arrangement may be such that at least the second sterilization treatment is not performed when the open state of the door 30 is being detected. Such an arrangement may prevent the inflow of the sterilizing material into the workroom 10 through the door 30 being accidentally open when an attempt is made to sterilize an article in the sterilization chamber 40 while work is going on in the workroom 10. Also, the arrangement may be such that when the open state of the door 30 is being detected, the first sterilization treatment and the second sterilization treatment are not performed, and when the closed state of the door 30 is being detected, the third sterilization treatment is not performed. Such an arrangement may prevent the inflow of the sterilizing material into the sterilization chamber 40 or the workroom 10 through the door 30 being accidentally open when, for instance, an attempt is made to sterilize the workroom 10 or the sterilization chamber 40 by conducting the first sterilization treatment or the second sterilization treatment, which may otherwise lead to an inadequate sterilization due to a low concentration of the sterilizing material. Also, this may prevent the situation in which when an attempt is made to sterilize both of the workroom 10 and the sterilization chamber 40 by conducting the third sterilization treatment, sterilization of only one of the workroom 10 and the sterilization chamber 40 is done because the door 30 is closed. Similarly, an opening/closing detection sensor may be provided at the front door 12 or the carry-in door 58 to control the execution of sterilization treatments according to the results of sensor detection.

What is claimed is:

1. An isolator comprising:
   a workroom in which a work involving biologically-derived materials is performed, said workroom including a first sterilizing material supply port, a first sterilizing material discharge port, a first gas supply port provided with a particulate trap filter, and a first gas discharge port provided with a particulate trap filter;
   a sterilization chamber for communicating with said workroom via a door in which an article to be carried into said workroom is sterilized, said sterilization chamber including a second sterilizing material supply port, a second sterilizing material discharge port, a second gas supply port provided with a particulate trap filter, and a second gas discharge port provided with a particulate trap filter;
   a sterilizing material supply unit for supplying a sterilizing material to said workroom and said sterilization chamber;
   a first sterilizing material supply path for connecting said sterilizing material supply unit to the workroom by way of the first sterilizing material supply port and without the medium of the particulate trap filter;
   a second sterilizing material supply path for connecting said sterilizing material supply unit to the second sterilizing material supply port without the medium of the particulate trap filter;
   a first circulating path for connecting the workroom to said sterilizing material supply unit by way of the first sterilizing material discharge port and without the medium of the particulate trap filter;
   a second circulating path for connecting the second sterilizing material discharge port to said sterilizing material supply unit without the medium of the particulate trap filter;
   a first gas supply path for connecting the exterior to the first gas supply port;
   a second gas supply path for connecting the exterior to the second gas supply port;
   a first gas discharge path for connecting the first gas discharge port to the exterior;
   a second gas discharge path for connecting the second gas discharge port to the exterior;
   a control unit for controlling the switching of flow paths for the sterilizing material and gas taken in from the exterior;
   a first filter circulating path, disposed exterior to the workroom, and connected to the first gas supply port and the first gas discharge port without passing through the sterilizing material supply unit, the first filter circulating path including a first circulator, the first filter circulating path separated from the first sterilizing material supply path and the first circulating path; and
   a second filter circulating path, disposed exterior to said sterilization chamber, and connected to the second gas supply port and the second gas discharge port without passing through the sterilizing material supply unit, the second filter circulating path including a second circulator, the second filter circulating path separated from the second sterilizing material supply path and the second circulating path.

2. An isolator according to claim 1, wherein a first sterilization treatment and a second sterilization treatment are executable independently of each other,
   the first sterilization treatment being such that the sterilizing material is supplied to said workroom through said first sterilizing material supply path when the door is closed, and
   the sterilizing material supplied into said workroom is circulated in the order of said first circulating path, said sterilizing material supply unit, said first sterilizing material supply path and said workroom, and is then discharged to said first gas discharge path from said workroom, and
   the second sterilization treatment being such that the sterilizing material is supplied to said sterilization chamber through said second sterilizing material supply path when the door is closed, and
   the sterilizing material supplied into said sterilization chamber is circulated in the order of said second circulating path, said sterilizing material supply unit, said second sterilizing material supply path and said sterilization chamber, and is then discharged to said second gas discharge path from said sterilization chamber.

3. An isolator according to claim 2, wherein executable is a third sterilization treatment in which the sterilizing material is supplied to said workroom and said sterilization chamber from said first sterilizing material supply path or said second sterilizing material supply path when the door is open, and
   the sterilizing material is sent to said sterilizing material supply unit from said second circulating path when said first sterilizing material supply path is used, or
   the sterilizing material is sent thereto from said first circulating path when said second sterilizing material supply path is used.

4. An isolator according to claim 3, wherein, in the third sterilization treatment, the sterilizing material is supplied to said workroom and said sterilization chamber through said first sterilizing material supply port, and
   sending out the sterilizing material to said sterilizing material supply unit through said second circulating path and sending out the sterilizing material thereto through said first circulating path are conducted in parallel with each other or in a switchable manner.

5. An isolator according to claim 2,
   wherein, in the first sterilization treatment, the sterilizing material supplied to said workroom is circulated with predetermined timing through said first filter circulating path, and
   wherein, in the second sterilization treatment, the sterilizing material supplied to said sterilization chamber is circulated with predetermined timing through said second filter circulating path.

6. An isolator according to claim 5, wherein said first filter circulating path includes a first decomposition treatment unit path that passes through a sterilizing material decomposition treatment unit having a catalyst for decomposing the sterilizing material, the sterilizing material decomposition treatment unit being configured to reduce the concentration of the sterilizing material to be discharged outside,
   wherein said second filter circulating path includes a second decomposition treatment unit path that passes through a sterilizing material decomposition treatment unit having a catalyst for decomposing the sterilizing material, the sterilizing material decomposition treatment unit being configured to reduce the concentration of the sterilizing material to be discharged outside,
   wherein, in the first sterilization treatment, the sterilizing material supplied to said workroom is circulated with predetermined timing through the first decomposition treatment unit path, and wherein, in the second sterilization treatment, the sterilizing material supplied to said sterilization chamber is circulated with predetermined timing through the second decomposition treatment unit path.

7. An isolator according to claim 1, wherein executable is a third sterilization treatment in which the sterilizing material is supplied to said workroom and said sterilization chamber from said first sterilizing material supply path or said second sterilizing material supply path when the door is open, and the sterilizing material is sent to said sterilizing material supply unit from said second circulating path when said first sterilizing material supply path is used, or the sterilizing material is sent thereto from said first circulating path when said second sterilizing material supply path is used.

8. An isolator according to claim 7, wherein, in the third sterilization treatment, the sterilizing material is supplied to said workroom and said sterilization chamber through said first sterilizing material supply port, and sending out the sterilizing material to said sterilizing material supply unit through said second circulating path and sending out the sterilizing material thereto through said first circulating path are conducted in parallel with each other or in a switchable manner.

* * * * *